(12) United States Patent
Liu

(10) Patent No.: US 11,375,909 B2
(45) Date of Patent: Jul. 5, 2022

(54) METHOD AND APPARATUS FOR DETERMINING PHYSIOLOGICAL PARAMETERS OF A SUBJECT, AND COMPUTER-PROGRAM PRODUCT THEREOF

(71) Applicant: BOE Technology Group Co., Ltd., Beijing (CN)

(72) Inventor: Cheng Liu, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 337 days.

(21) Appl. No.: 16/626,303

(22) PCT Filed: Dec. 5, 2018

(86) PCT No.: PCT/CN2018/119357
§ 371 (c)(1),
(2) Date: Dec. 23, 2019

(87) PCT Pub. No.: WO2020/113466
PCT Pub. Date: Jun. 11, 2020

(65) Prior Publication Data
US 2021/0353167 A1  Nov. 18, 2021

(51) Int. Cl.
*A61B 5/024* (2006.01)
*G06T 7/90* (2017.01)
(Continued)

(52) U.S. Cl.
CPC ........ *A61B 5/02416* (2013.01); *A61B 5/0082* (2013.01); *A61B 5/14551* (2013.01);
(Continued)

(58) Field of Classification Search
CPC ......... A61B 5/00; A61B 5/0082; A61B 5/004; A61B 5/02416; A61B 5/14551;
(Continued)

(56) References Cited

U.S. PATENT DOCUMENTS

| 6,728,561 B2 | 4/2004 | Smith et al. |
| 2007/0219439 A1 | 9/2007 | Vilser et al. |

(Continued)

FOREIGN PATENT DOCUMENTS

| CN | 103617419 A | 3/2014 |
| CN | 103839052 A | 6/2014 |

(Continued)

OTHER PUBLICATIONS

International Search Report & Written Opinion dated Sep. 6, 2019, regarding PCT/CN2018/119357.

*Primary Examiner* — Brenda C Bernardi
(74) *Attorney, Agent, or Firm* — Intellectual Valley Law, P.C.

(57) ABSTRACT

A method for determining one or more physiological parameters of a subject. The method includes providing a plurality of images of a vessel of the subject in response to illumination of the vessel to light of different wavelengths; converting each of the plurality of images of the vessel into at least two grayscale images, thereby generating a plurality of first grayscale images of a first wavelength range and a plurality of second grayscale images of a second wavelength range, the first wavelength range and the second wavelength range being different from each other; and determining the one or more physiological parameters of the subject based on at least the plurality of first grayscale images and the plurality of second grayscale images.

18 Claims, 5 Drawing Sheets providing a plurality of images of a vessel of the subject in response to illumination of the vessel to light of different wavelengths converting each of the plurality of images of the vessel into at least two grayscale images, thereby generating a plurality of first grayscale images of a first wavelength range and a plurality of second grayscale images of a second wavelength range, the first wavelength range and the second wavelength range being different from each other determining the one or more physiological parameters of the subject based on at least the plurality of first grayscale images and the plurality of second grayscale images

(51) Int. Cl.
*A61B 5/00* (2006.01)
*A61B 5/1455* (2006.01)
*G06T 7/00* (2017.01)
*G06V 10/143* (2022.01)

(52) U.S. Cl.
CPC .............. *G06T 7/0014* (2013.01); *G06T 7/90* (2017.01); *G06V 10/143* (2022.01); *G06T 2207/10024* (2013.01); *G06T 2207/10048* (2013.01); *G06T 2207/30101* (2013.01); *G06V 2201/03* (2022.01)

(58) Field of Classification Search
CPC ..... A61B 5/0059; A61B 5/02433; G06T 7/90; G06T 7/0014; G06T 2207/30101; G06T 2207/10048; G06T 2207/10024; G06K 9/2018; G06K 2209/05
See application file for complete search history.

(56) References Cited

U.S. PATENT DOCUMENTS

| | | |
|---|---|---|
| 2008/0170228 A1 | 7/2008 | Jiang |
| 2012/0197133 A1 | 8/2012 | Li et al. |
| 2016/0117563 A1 | 4/2016 | Shin et al. |

FOREIGN PATENT DOCUMENTS

| | | | |
|---|---|---|---|
| CN | 103870704 A | | 6/2014 |
| CN | 104085371 A | | 10/2014 |
| CN | 103006238 B | | 11/2014 |
| CN | 104997519 A | * | 10/2015 |
| CN | 104997519 A | | 10/2015 |
| CN | 106264467 A | | 1/2017 |
| CN | 107194367 A | | 9/2017 |
| CN | 107510461 A | | 12/2017 |

* cited by examiner providing a plurality of images of a vessel of the subject in response to illumination of the vessel to light of different wavelengths converting each of the plurality of images of the vessel into at least two grayscale images, thereby generating a plurality of first grayscale images of a first wavelength range and a plurality of second grayscale images of a second wavelength range, the first wavelength range and the second wavelength range being different from each other determining the one or more physiological parameters of the subject based on at least the plurality of first grayscale images and the plurality of second grayscale images

FIG. 1 determining a first value of a first color component, a second value of a second color component, and a third value of a third color component for each pixel of a plurality of pixels of each of the plurality of images determining a first light intensity in the first wavelength range and a second light intensity in the second wavelength range for each pixel of the plurality of pixels, based on the first value, the second value, and the third value generating the plurality of first grayscale images of the first wavelength range based on the first light intensity in each pixel of the plurality of pixels and the plurality of second grayscale images of the second wavelength range based on the second light intensity in each pixel of the plurality of pixels

FIG. 2

METHOD AND APPARATUS FOR DETERMINING PHYSIOLOGICAL PARAMETERS OF A SUBJECT, AND COMPUTER-PROGRAM PRODUCT THEREOF

CROSS-REFERENCE TO RELATED APPLICATION

This application is a national stage application under 35 U.S.C. § 371 of International Application No. PCT/CN2018/119357, filed Dec. 5, 2018, the contents of which are incorporated by reference in the entirety.

TECHNICAL FIELD

The present invention relates to medical device technology, more particularly, to a method and an apparatus for determining one or more physiological parameters of a subject, and a computer-program product thereof.

BACKGROUND

Optical imaging is an emerging technology with potential for improving disease prevention, diagnosis, and treatment in the medical office, at the bedside, or in the operating room. Optical imaging technologies can noninvasively differentiate among soft tissues, and between native soft tissues and tissue labeled with either endogenous or exogenous contrast media, using their different photon absorption or scattering profiles at different wavelengths. Such photon absorption and scattering differences offers potential for providing specific tissue contrasts, and enables studying functional and molecular level activities that are the basis for health and disease.

SUMMARY

In one aspect, the present invention provides a method for determining one or more physiological parameters of a subject, comprising providing a plurality of images of a vessel of the subject in response to illumination of the vessel to light of different wavelengths; converting each of the plurality of images of the vessel into at least two grayscale images, thereby generating a plurality of first grayscale images of a first wavelength range and a plurality of second grayscale images of a second wavelength range, the first wavelength range and the second wavelength range being different from each other; and determining the one or more physiological parameters of the subject based on at least the plurality of first grayscale images and the plurality of second grayscale images.

Optionally, converting each of the plurality of images of the vessel into at least two grayscale images comprises determining a first value of a first color component, a second value of a second color component, and a third value of a third color component for each pixel of a plurality of pixels of each of the plurality of images; determining a first light intensity in the first wavelength range and a second light intensity in the second wavelength range for each pixel of the plurality of pixels, based on the first value, the second value, and the third value; and generating the plurality of first grayscale images of the first wavelength range based on the first light intensity in each pixel of the plurality of pixels and the plurality of second grayscale images of the second wavelength range based on the second light intensity in each pixel of the plurality of pixels.

Optionally, determining the first light intensity in the first wavelength range and the second light intensity in the second wavelength range is performed based on Equation (1):

$$\begin{cases} Q_{1R}I_1^{mn} + Q_{2R}I_2^{mn} = e^{\left(\frac{V_R^{mn}}{K_R}\right)} \\ Q_{1G}I_1^{mn} + Q_{2G}I_2^{mn} = e^{\left(\frac{V_G^{mn}}{K_G}\right)} ; \\ Q_{1B}I_1^{mn} + Q_{2B}I_2^{mn} = e^{\left(\frac{V_B^{mn}}{K_B}\right)} \end{cases} \quad (1)$$

wherein $V_R^{mn}$ stands for the first value of a first color component for a pixel (m, n) in a plurality of pixels having m rows and n columns of pixels, $V_G^{mn}$ stands for the second value of a second color component for the pixel (m, n), $V_B^{mn}$ stands for the third value of a third color component for the pixel (m, n), $Q_{1R}$ stands for a first reference quantum efficiency of the first color component of the pixel (m, n) within the first wavelength range, $Q_{1G}$ stands for a second reference quantum efficiency of the second color component of the pixel (m, n) within the first wavelength range, $Q_{1B}$ stands for a third reference quantum efficiency of the third color component of the pixel (m, n) within the first wavelength range, $Q_{2R}$ stands for a fourth reference quantum efficiency of the first color component of the pixel (m, n) within the second wavelength range, $Q_{2G}$ stands for a fifth reference quantum efficiency of the second color component of the pixel (m, n) within the second wavelength range, $Q_{2B}$ stands for a sixth reference quantum efficiency of the third color component of the pixel (m, n) within the second wavelength range, $I_1^{mn}$ stands for the first light intensity in the first wavelength range for the pixel (m, n), $I_2^{mn}$ stands for the second light intensity in the second wavelength range for the pixel (m, n), $K_R$ is a constant coefficient for the first color component of the pixel (m, n), $K_G$ is a constant coefficient for the second color component of the pixel (m, n), and $K_B$ is a constant coefficient for the third color component of the pixel (m, n).

Optionally, converting each of the plurality of images of the vessel into at least two grayscale images comprises converting each of the plurality of images of the vessel into three grayscale images, thereby generating the plurality of first grayscale images of the first wavelength range, the plurality of second grayscale images of the second wavelength range, and a plurality of third grayscale images of a third wavelength range, the first wavelength range, the second wavelength range, and the third wavelength range being different from each other; and wherein determining the one or more physiological parameters of the subject based on at least the plurality of first grayscale images and the plurality of second grayscale images comprises determining at least two physiological parameters of the subject based on the plurality of first grayscale images, the plurality of second grayscale images, and the plurality of third grayscale images.

Optionally, converting each of the plurality of images of the vessel into three grayscale images comprises determining a first value of a first color component, a second value of a second color component, and a third value of a third color component for each pixel of a plurality of pixels of each of the plurality of images; determining a first light intensity in the first wavelength range, a second light intensity in the second wavelength range, and a third light intensity in the third wavelength range for each pixel of the plurality of pixels, based on the first value, the second value, and the third value; and generating the plurality of first grayscale images of the first wavelength range based on the first light intensity in each pixel of the plurality of pixels, the plurality of second grayscale images of the second wavelength range based on the second light intensity in each pixel of the plurality of pixels, and the plurality of third grayscale images of the third wavelength range based on the third light intensity in each pixel of the plurality of pixels.

Optionally, determining the first light intensity in the first wavelength range, the second light intensity in the second wavelength range, and the third light intensity in the third wavelength range is performed based on Equation (2):

$$\begin{cases} Q_{1R}I_1^{mn} + Q_{2R}I_2^{mn} + Q_{3R}I_3^{mn} = e^{\left(\frac{V_R^{mn}}{K_R}\right)} \\ Q_{1G}I_1^{mn} + Q_{2G}I_2^{mn} + Q_{3G}I_3^{mn} = e^{\left(\frac{V_G^{mn}}{K_G}\right)} ; \\ Q_{1B}I_1^{mn} + Q_{2B}I_2^{mn} + Q_{3B}I_3^{mn} = e^{\left(\frac{V_B^{mn}}{K_B}\right)} \end{cases} \quad (2)$$

wherein $V_R^{mn}$ stands for the first value of a first color component for a pixel (m, n) in a plurality of pixels having m rows and n columns of pixels, $V_G^{mn}$ stands for the second value of a second color component for the pixel (m, n), $V_B^{mn}$ stands for the third value of a third color component for the pixel (m, n), $Q_{1R}$ stands for a first reference quantum efficiency of the first color component of the pixel (m, n) within the first wavelength range, $Q_{1G}$ stands for a second reference quantum efficiency of the second color component of the pixel (m, n) within the first wavelength range, $Q_{1B}$ stands for a third reference quantum efficiency of the third color component of the pixel (m, n) within the first wavelength range, $Q_{2R}$ stands for a fourth reference quantum efficiency of the first color component of the pixel (m, n) within the second wavelength range, $Q_{2G}$ stands for a fifth reference quantum efficiency of the second color component of the pixel (m, n) within the second wavelength range, $Q_{2B}$ stands for a sixth reference quantum efficiency of the third color component of the pixel (m, n) within the second wavelength range, $Q_{3R}$ stands for a seventh reference quantum efficiency of the first color component of the pixel (m, n) within the third wavelength range, $Q_{3G}$ stands for an eighth reference quantum efficiency of the second color component of the pixel (m, n) within the third wavelength range, $Q_{3B}$ stands for a ninth reference quantum efficiency of the third color component of the pixel (m, n) within the third wavelength range, $I_1^{mn}$ stands for the first light intensity in the first wavelength range for the pixel (m, n), $I_2^{mn}$ stands for the second light intensity in the second wavelength range for the pixel (m, n), $I_3^{mn}$ stands for the third light intensity in the third wavelength range for the pixel (m, n), $K_R$ is a constant coefficient for the first color component of the pixel (m, n), $K_G$ is a constant coefficient for the second color component of the pixel (m, n), and $K_B$ is a constant coefficient for the third color component of the pixel (m, n).

Optionally, the method further comprises illuminating the vessel of the subject with a compound light having a first light of the first wavelength range, a second light of the second wavelength range, a third light of the third wavelength range; and detecting light reflected by or transmitted through a body part of the subject using an image sensor, thereby generating the plurality of images of the vessel of the subject.

Optionally, the method further comprises at least one of (1) illuminating the vessel of the subject with a first reference light of the first wavelength range and determining a first reference quantum efficiency of the first color component of a pixel within the first wavelength range, a second reference quantum efficiency of the second color component of the pixel within the first wavelength range, and a third reference quantum efficiency of the third color component of the pixel within the first wavelength range; (2) illuminating the vessel of the subject with a second reference light of the second wavelength range and determining a fourth reference quantum efficiency of the first color component of the pixel within the second wavelength range, a fifth reference quantum efficiency of the second color component of the pixel within the second wavelength range, and a sixth reference quantum efficiency of the third color component of the pixel within the second wavelength range; or (3) illuminating the vessel of the subject with a third reference light of a third wavelength range and determining a seventh reference quantum efficiency of the first color component of the pixel within the third wavelength range, an eighth reference quantum efficiency of the second color component of the pixel within the third wavelength range, and a ninth reference quantum efficiency of the third color component of the pixel within the third wavelength range.

Optionally, the first wavelength range and the second wavelength range are in a wavelength range of near infrared light and visible light.

Optionally, the first wavelength range is between approximately 760 nm and approximately 850 nm; the second wavelength range is between approximately 850 nm and approximately 960 nm; and the third wavelength range is between approximately 530 nm and approximately 660 nm.

Optionally, the one or more physiological parameters of the subject comprise a vein pattern, a pulse wave signal, and a blood oxygen level of the subject.

In another aspect, the present invention provides an apparatus for measuring one or more physiological parameters of a subject using a plurality of images of a vessel of the subject provided in response to illumination of the vessel to light of different wavelengths, comprising a memory; and one or more processors; wherein the memory and the one or more processors are connected with each other; and the memory stores computer-executable instructions for controlling the one or more processors to convert each of the plurality of images of the vessel into at least two grayscale images, thereby generating a plurality of first grayscale images of a first wavelength range and a plurality of second grayscale images of a second wavelength range, the first wavelength range and the second wavelength range being different from each other; and determine the one or more physiological parameters of the subject based on at least the plurality of first grayscale images and the plurality of second grayscale images.

Optionally, the apparatus further comprises a light source configured to illuminate a vessel of the subject with a compound light having at least a first light of the first wavelength range and a second light of the second wavelength range; and an image sensor configured to detecting the compound light reflected by or transmitted through a body part of the subject, thereby generating the plurality of images of the vessel of the subject.

Optionally, the image sensor is a single image sensor capable of detecting the compound light having the first light of the first wavelength range and the second light of the second wavelength range.

Optionally, the light source is a single light source capable of simultaneously emitting the first light of the first wavelength range and the second light of the second wavelength range.

Optionally, the memory further stores computer-executable instructions for controlling the one or more processors to determine a first value of a first color component, a second value of a second color component, and a third value of a third color component for each pixel of a plurality of pixels of each of the plurality of images; determine a first light intensity in the first wavelength range and a second light intensity in the second wavelength range for each pixel of the plurality of pixels, based on the first value, the second value, and the third value; and generate the plurality of first grayscale images of the first wavelength range based on the first light intensity in each pixel of the plurality of pixels and the plurality of second grayscale images of the second wavelength range based on the second light intensity in each pixel of the plurality of pixels.

Optionally, the memory further stores computer-executable instructions for controlling the one or more processors to convert each of the plurality of images of the vessel into three grayscale images, thereby generating the plurality of first grayscale images of the first wavelength range, the plurality of second grayscale images of the second wavelength range, and a plurality of third grayscale images of a third wavelength range, the first wavelength range, the second wavelength range, and the third wavelength range being different from each other; and determining at least two physiological parameters of the subject based on the plurality of first grayscale images, the plurality of second grayscale images, and the plurality of third grayscale images.

Optionally, the memory further stores computer-executable instructions for controlling the one or more processors to determine a first value of a first color component, a second value of a second color component, and a third value of a third color component for each pixel of a plurality of pixels of each of the plurality of images; determine a first light intensity in the first wavelength range, a second light intensity in the second wavelength range, and a third light intensity in the third wavelength range for each pixel of the plurality of pixels, based on the first value, the second value, and the third value; and generate the plurality of first grayscale images of the first wavelength range based on the first light intensity in each pixel of the plurality of pixels, the plurality of second grayscale images of the second wavelength range based on the second light intensity in each pixel of the plurality of pixels, and the plurality of third grayscale images of third wavelength range based on the third light intensity in each pixel of the plurality of pixels.

Optionally, the one or more physiological parameters of the subject comprise a vein pattern, a pulse wave signal, and a blood oxygen level of the subject.

In another aspect, the present invention provides a computer-program product comprising a non-transitory tangible computer-readable medium having computer-readable instructions thereon, the computer-readable instructions being executable by a processor to cause the processor to perform converting each of a plurality of images of a vessel of a subject provided in response to illumination of the vessel to light of different wavelengths into at least two grayscale images, thereby generating a plurality of first grayscale images of a first wavelength range and a plurality of second grayscale images of a second wavelength range, the first wavelength range and the second wavelength range being different from each other; and determining one or more physiological parameters of the subject based on at least the plurality of first grayscale images and the plurality of second grayscale images.

BRIEF DESCRIPTION OF THE FIGURES

The following drawings are merely examples for illustrative purposes according to various disclosed embodiments and are not intended to limit the scope of the present invention.

FIG. 1 is a flow chart illustrating a method for determining one or more physiological parameters of a subject in some embodiments according to the present disclosure.

FIG. 2 is a flow chart illustrating a method for determining one or more physiological parameters of a subject in some embodiments according to the present disclosure.

DETAILED DESCRIPTION

Figure 3:
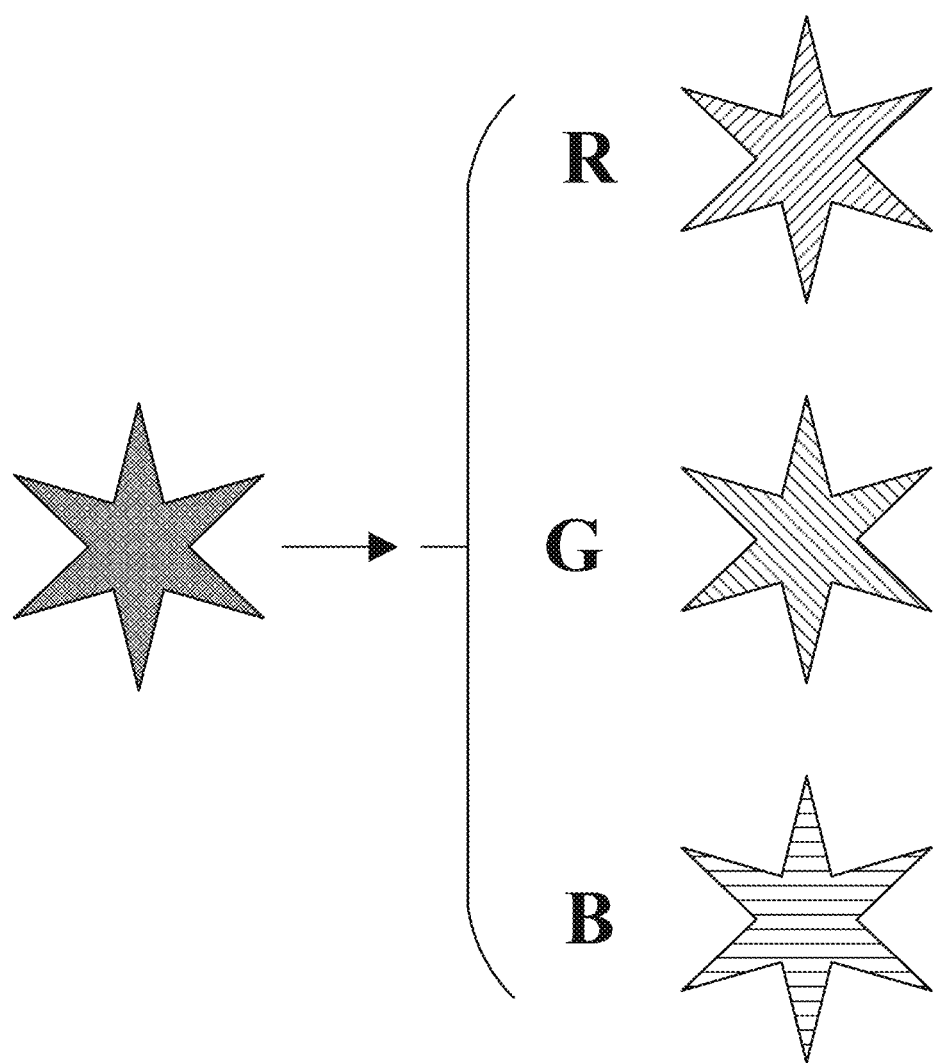
FIG. 3 is a schematic diagram illustrating an RGB channel separation of an image in some embodiments according to the present disclosure.

The disclosure will now be described more specifically with reference to the following embodiments. It is to be noted that the following descriptions of some embodiments are presented herein for purpose of illustration and description only. It is not intended to be exhaustive or to be limited to the precise form disclosed.

Various apparatuses have been developed to detect physiological parameters of a subject. However, to measure multiple physiological parameters of the subject, it is required to take the measurements several times to obtain distinct biometric signals for each of the measurements, resulting in poor user experience. Even if multiple apparatuses are integrated into a device, these apparatuses still require separate set-ups, such as separate light sources and separate sensors. Thus, the manufacturing costs remains high, and it is difficult to miniaturize the device.

Accordingly, the present disclosure provides, inter alia, a method for determining one or more physiological parameters of a subject, an apparatus for determining one or more physiological parameters of a subject, and a computer-program product thereof that substantially obviate one or more of the problems due to limitations and disadvantages of the related art. In one aspect, the present disclosure provides a method for determining one or more physiological parameters of a subject. FIG. 1 is a flow chart illustrating a method for determining one or more physiological parameters of a subject in some embodiments according to the present disclosure. Referring to FIG. 1, the method in some embodiments includes providing a plurality of images of a vessel of the subject in response to illumination of the vessel to light of different wavelengths; converting each of the plurality of images of the vessel into at least two grayscale images, thereby generating a plurality of first grayscale images of a first wavelength range and a plurality of second grayscale images of a second wavelength range, the first wavelength range and the second wavelength range being different from each other; and determining the one or more physiological parameters of the subject based on at least the plurality of first grayscale images and the plurality of second grayscale images. As referred to herein, the term "physiological parameter" refers a health-related parameter of the subject. A physiological parameter may be directly and/or indirectly measured, detected and/or derived from a measurement of a device, for example, via a sensor. In some embodiments, the physiological parameter may include such parameters as, but not limited to blood related parameters, such as, vein pattern, pulse wave parameters (e.g., pulse wave velocity, pulse rate, pulse transit time), blood chemical level (e.g., blood oxygen level, blood cholesterol level, blood glucose level), blood pressure, heart rate, or combinations thereof. As used herein, the term "vessel" comprises any conduit and includes an artery or vein. As used herein, the term "subject" refers to a mammal, including both human and other mammals.

Optionally, the first wavelength range and the second wavelength range are non-overlapping ranges. Optionally, the first wavelength range and the second wavelength range are partially overlapping ranges.

FIG. 2 is a flow chart illustrating a method for determining one or more physiological parameters of a subject in some embodiments according to the present disclosure. Referring to FIG. 2, the step of converting each of the plurality of images of the vessel into at least two grayscale images in some embodiments includes determining a first value of a first color component, a second value of a second color component, and a third value of a third color component for each pixel of a plurality of pixels of each of the plurality of images; determining a first light intensity in the first wavelength range and a second light intensity in the second wavelength range for each pixel of the plurality of pixels, based on the first value, the second value, and the third value; and generating the plurality of first grayscale images of the first wavelength range based on the first light intensity in each pixel of the plurality of pixels and the plurality of second grayscale images of the second wavelength range based on the second light intensity in each pixel of the plurality of pixels.

For example, the first color component, the second color component, and the third color component of the pixel may be a red component, a green component, and a blue component of the image in the pixel. FIG. 3 is a schematic diagram illustrating an RGB channel separation of an image in some embodiments according to the present disclosure. The image in each pixel of the plurality of pixels is separated into three color channels, e.g., a red color channel (R), a green color channel (G), and a blue color channel (B). The first value for the red component, the second value for the green component, and the third value for the blue component, are determined. In one example, the first value, the second value, and the third value can be represented by grayscale values of the red color channel, the green color channel, and the blue color channel. Based on the first value, the second value, and the third value, the first light intensity in the first wavelength range and the second light intensity in the second wavelength range, for each pixel of the plurality of pixels, are determined. Optionally, the first wavelength range and the second wavelength range are in a wavelength range of near infrared light and visible light. In one example, the first wavelength range is a wavelength range of a near infrared light, and the second wavelength range is a wavelength range of a visible light. In another example, the first wavelength range is a wavelength range of a near infrared light, and the second wavelength range is a wavelength range of a near infrared light. Optionally, the first wavelength range is between approximately 760 nm and approximately 850 nm; and the second wavelength range is between approximately 850 nm and approximately 960 nm. Optionally, the first wavelength range is between approximately 760 nm and approximately 850 nm; and the second wavelength range is between approximately 530 nm and approximately 660 nm. Optionally, the first wavelength range is between approximately 850 nm and approximately 960 nm; and the second wavelength range is between approximately 530 nm and approximately 660 nm. Once the first light intensity in the first wavelength range for each pixel is determined, the plurality of first grayscale images of the first wavelength range can be generated. Once the second light intensity in the second wavelength range for each pixel is determined, the plurality of second grayscale images can be generated.

Figure 4:
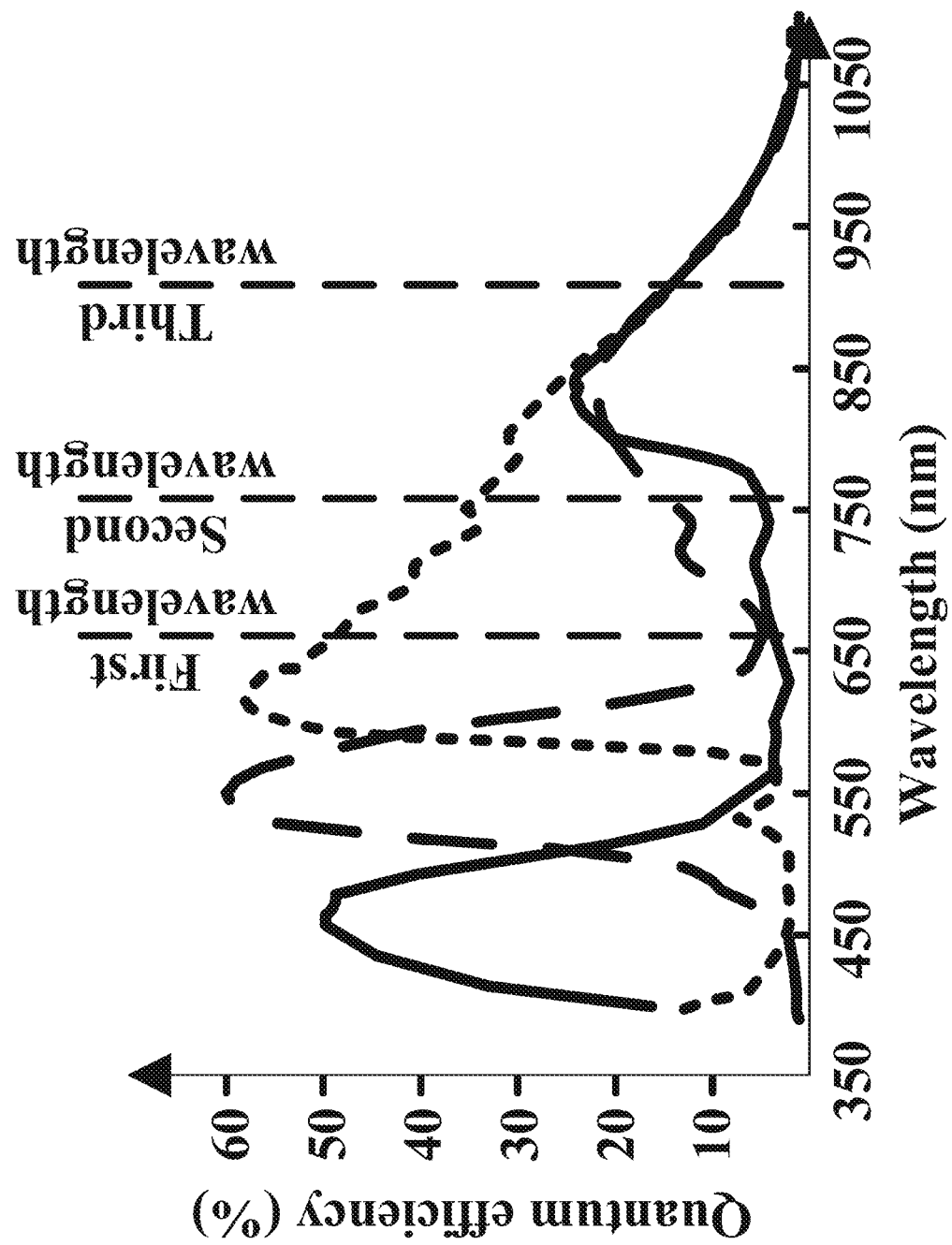
FIG. 4 depicts a curve of quantum efficiency over a wavelength range between 350 nm and 1050 nm of an image recorded for a first color component of a pixel (the densely dotted line), a second color component of the pixel (the sparsely dotted line), and a third color component of the pixel (the solid line) in some embodiments according to the present disclosure.

FIG. 4 depicts a curve of quantum efficiency over a wavelength range between 350 nm and 1050 nm of an image recorded for a first color component of a pixel (the densely dotted line), a second color component of the pixel (the sparsely dotted line), and a third color component of the pixel (the solid line) in some embodiments according to the present disclosure. Referring to FIG. 4, variation of quantum efficiency of a first color component of the pixel over a wavelength range from 350 nm to 1050 nm is shown as the densely dotted line; variation of quantum efficiency of a second color component of the pixel over a wavelength range from 350 nm to 1050 nm is shown as the sparsely dotted line; and variation of quantum efficiency of a third color component of the pixel over a wavelength range from 350 nm to 1050 nm is shown as the solid line.

With reference to each reference light (e.g., each of the first reference light, the second reference light, and the third reference light), a quantum efficiency of a color component of the pixel at a particular wavelength is a fixed value. For example, and referring to FIG. 4, Quantum efficiencies of the first color component of the pixel respectively at the first wavelength, the second wavelength, and the third wavelength are fixed values. Similarly, quantum efficiencies of the second color component of the pixel respectively at the first wavelength, the second wavelength, and the third wavelength are fixed values; and quantum efficiencies of the third color component of the pixel respectively at the first wavelength, the second wavelength, and the third wavelength are fixed values. These quantum efficiencies can be predetermined, e.g., using each individual reference light as a calibration.

In some embodiments, the first light intensity in the first wavelength range and the second light intensity in the second wavelength range can be determined based on Equation (1):

$$\begin{cases} Q_{1R}I_1^{mn} + Q_{2R}I_2^{mn} = e^{\left(\frac{V_R^{mn}}{K_R}\right)} \\ Q_{1G}I_1^{mn} + Q_{2G}I_2^{mn} = e^{\left(\frac{V_G^{mn}}{K_G}\right)} \\ Q_{1B}I_1^{mn} + Q_{2B}I_2^{mn} = e^{\left(\frac{V_B^{mn}}{K_B}\right)} \end{cases} \quad (1)$$

wherein $V_R^{mn}$ stands for the first value of a first color component for a pixel (m, n) in a plurality of pixels having m rows and n columns of pixels, $V_G^{mn}$ stands for the second value of a second color component for the pixel (m, n), $V_B^{mn}$ stands for the third value of a third color component for the pixel (m, n), $Q_{1R}$ stands for a first reference quantum efficiency of the first color component of the pixel (m, n) within the first wavelength range, $Q_{1G}$ stands for a second reference quantum efficiency of the second color component of the pixel (m, n) within the first wavelength range, $Q_{1B}$ stands for a third reference quantum efficiency of the third color component of the pixel (in, n) within the first wavelength range, $Q_{2R}$ stands for a fourth reference quantum efficiency of the first color component of the pixel (m, n) within the second wavelength range, $Q_{2G}$ stands for a fifth reference quantum efficiency of the second color component of the pixel (m, n) within the second wavelength range, $Q_{2B}$ stands for a sixth reference quantum efficiency of the third color component of the pixel (m, n) within the second wavelength range, $I_1^{mn}$ stands for the first light intensity in the first wavelength range for the pixel (m, n), $I_2^{mn}$ stands for the second light intensity in the second wavelength range for the pixel (m, n), $K_R$ is a constant coefficient for the first color component of the pixel (m, n), $K_G$ is a constant coefficient for the second color component of the pixel (m, n), and $K_B$ is a constant coefficient for the third color component of the pixel (m, n).

As discussed above, $Q_{1R}$, $Q_{1G}$, $Q_{1B}$, $Q_{2R}$, $Q_{2G}$, and $Q_{2B}$ are fixed values, and may be obtained by a calibration test. The three values $V_R^{mn}$, $V_G^{mn}$, and $V_B^{mn}$ may be measured by separating the image in each pixel of the plurality of pixels into three different color channels (e.g., a red color channel, a green color channel, and a blue color channel). Optionally, $V_R^{mn}$, $V_G^{mn}$, and $V_B^{mn}$ may be represented by grayscale values. Based on Equation (1), the first light intensity in the first wavelength range for the pixel (m, n), $I_1^{mn}$, and the second light intensity in the second wavelength range for the pixel (m, n), $I_2^{mn}$, can be determined.

In some embodiments, an image sensor is used to detect a compound light reflected by or transmitted through a body part of the subject, thereby generating the plurality of images of the vessel of the subject. In determining the first light intensity in the first wavelength range and the second light intensity in the second wavelength range, parameters of the image sensor are maintained substantially unchanged. For example, parameters affecting the RGB values of an output image of the image sensor, including aperture, exposure time, focal length, and gain, are maintained substantially unchanged in the process of determining the first light intensity and the second light intensity. Frame rate can be adjusted as long as the frame interval is greater than the exposure time.

Constant coefficient $K_R$, $K_G$, and $K_B$ are independent of the wavelength. These constant coefficients are determined by several wavelength-independent factors such as pixel area, exposure time, amplification gain, and tuning algorithm. Optionally, the constant coefficients may be determined by calibration. For example, the constant coefficient $K_R$ can be determined based on Equation (2):

$$K_R = \frac{V_{R0}}{\ln(Q_{0R}I_0)}; \quad (2)$$

wherein $Q_{0R}$ stands for a reference quantum efficiency of the first color component of the pixel at a reference wavelength, $I_0$ stands for a light intensity at the reference wavelength for the pixel, $V_{R0}$ stands for a reference value (e.g., a grayscale value) of the first color component for the pixel. The constant coefficients $K_G$ and $K_B$ can be determined in a similar fashion.

Equation (1) can be expressed as follows:

$$\tilde{Q}\tilde{I}^{mn} = e^{\begin{pmatrix}\frac{V_R^{mn}}{K_R}\\ \frac{V_G^{mn}}{K_G}\\ \frac{V_B^{mn}}{K_B}\end{pmatrix}^{mn}}, \tilde{Q} = \begin{pmatrix}Q_{1R} & Q_{2R}\\ Q_{1G} & Q_{2G}\\ Q_{1B} & Q_{2B}\end{pmatrix}, \tilde{I} = \begin{pmatrix}I_1\\ I_2\end{pmatrix}. \quad (3)$$

An optimal solution for $\tilde{I}^{mn}$ may be obtained such that a residual error $E(\tilde{I}^{mn})$ is minimized, wherein the residual error can be expressed as:

$$E(\tilde{I}^{mn}) = \left\| \tilde{Q}\tilde{I}^{mn} = e^{\begin{pmatrix}\frac{V_R^{mn}}{K_R}\\ \frac{V_G^{mn}}{K_G}\\ \frac{V_B^{mn}}{K_B}\end{pmatrix}^{mn}} \right\|. \quad (4)$$

Upon determination of the first light intensity in the first wavelength range and the second light intensity in the second wavelength range for each pixel of the plurality of pixels, the plurality of first grayscale images of the first wavelength range and the plurality of second grayscale images of the second wavelength range can be generated. The plurality of first grayscale images and the plurality of second grayscale images can then be used for determining one or more physiological parameters of the subject. In one example, the plurality of first grayscale images and the plurality of second grayscale images are used to determine a blood oxygen level of the subject. In another example, the plurality of first grayscale images are used to determine a vein pattern of the subject, and the plurality of second grayscale images are used to determine a pulse wave signal of the subject.

In some embodiments, the method includes converting each of the plurality of images of the vessel into three grayscale images, thereby generating the plurality of first grayscale images of the first wavelength range, the plurality of second grayscale images of the second wavelength range, and a plurality of third grayscale images of a third wavelength range. The first wavelength range, the second wavelength range, and the third wavelength range are different from each other. Optionally, any two ranges of the first wavelength range, the second wavelength range, and the third wavelength range are non-overlapping with respect to each other. Optionally, two ranges of the first wavelength range, the second wavelength range, and the third wavelength range are partially overlapping with respect to each other. Optionally, the first wavelength range, the second wavelength range, and the third wavelength range are partially overlapping with respect to each other.

The one or more physiological parameters of the subject are determined based on the plurality of first grayscale images, the plurality of second grayscale images, and the plurality of third grayscale images.

In some embodiments, the step of converting each of the plurality of images of the vessel into three grayscale images includes determining a first value of a first color component, a second value of a second color component, and a third value of a third color component for each pixel of a plurality of pixels of each of the plurality of images; determining a first light intensity in the first wavelength range, a second light intensity in the second wavelength range, and a third light intensity in the third wavelength range for each pixel of the plurality of pixels, based on the first value, the second value, and the third value; and generating the plurality of first grayscale images of the first wavelength range based on the first light intensity in each pixel of the plurality of pixels, the plurality of second grayscale images of the second wavelength range based on the second light intensity in each pixel of the plurality of pixels, and the plurality of third grayscale images of the third wavelength range based on the third light intensity in each pixel of the plurality of pixels.

For example, the first color component, the second color component, and the third color component of the pixel may be a red component, a green component, and a blue component of the image in the pixel. The image in each pixel of the plurality of pixels is separated into three color channels, e.g., a red color channel, a green color channel, and a blue color channel. The first value for the red component, the second value for the green component, and the third value for the blue component, are determined. Based on the first value, the second value, and the third value, the first light intensity in the first wavelength range, the second light intensity in the second wavelength range, and the third light intensity in the third wavelength range, for each pixel of the plurality of pixels, are then determined. Optionally, the first wavelength range and the second wavelength range are in a wavelength range of near infrared light, and the third wavelength range is in a wavelength range of visible light. Optionally, the first wavelength range is between approximately 760 nm and approximately 850 nm, the second wavelength range is between approximately 850 nm and approximately 960 nm, and the third wavelength range is between approximately 530 nm and approximately 660 nm. Once the first light intensity in the first wavelength range for each pixel is determined, the plurality of first grayscale images of the first wavelength range can be generated. Once the second light intensity in the second wavelength range for each pixel is determined, the plurality of second grayscale images can be generated. Once the third light intensity in the third wavelength range for each pixel is determined, the plurality of third grayscale images can be generated.

In some embodiments, the first light intensity in the first wavelength range, the second light intensity in the second wavelength range, and the third light intensity in the third wavelength range can be determined based on Equation (5):

$$\begin{cases} Q_{1R}I_1^{mn} + Q_{2R}I_2^{mn} + Q_{3R}I_3^{mn} = e^{\left(\frac{V_R^{mn}}{K_R}\right)} \\ Q_{1G}I_1^{mn} + Q_{2G}I_2^{mn} + Q_{3G}I_3^{mn} = e^{\left(\frac{V_G^{mn}}{K_G}\right)} \\ Q_{1B}I_1^{mn} + Q_{2B}I_2^{mn} + Q_{3B}I_3^{mn} = e^{\left(\frac{V_B^{mn}}{K_B}\right)} \end{cases} \quad (5)$$

wherein $V_R^{mn}$ stands for the first value of a first color component for a pixel (m, n) in a plurality of pixels having m rows and n columns of pixels, $V_G^{mn}$ stands for the second value of a second color component for the pixel (m, n), $V_B^{mn}$ stands for the third value of a third color component for the pixel (m, n), $Q_{1R}$ stands for a first reference quantum efficiency of the first color component of the pixel (m, n) within the first wavelength range, $Q_{1G}$ stands for a second reference quantum efficiency of the second color component of the pixel (m, n) within the first wavelength range, $Q_{1B}$ stands for a third reference quantum efficiency of the third color component of the pixel (m, n) within the first wavelength range, $Q_{2R}$ stands for a fourth reference quantum efficiency of the first color component of the pixel (m, n) within the second wavelength range, $Q_{2G}$ stands for a fifth reference quantum efficiency of the second color component of the pixel (m, n) within the second wavelength range, $Q_{2B}$ stands for a sixth reference quantum efficiency of the third color component of the pixel (m, n) within the second wavelength range, $Q_{3R}$ stands for a seventh reference quantum efficiency of the first color component of the pixel (m, n) within the third wavelength range, $Q_{3G}$ stands for an eighth reference quantum efficiency of the second color component of the pixel (m, n) within the third wavelength range, $Q_{3B}$ stands for a ninth reference quantum efficiency of the third color component of the pixel (m, n) within the third wavelength range, $I_1^{mn}$ stands for the first light intensity in the first wavelength range for the pixel (m, n), $I_2^{mn}$ stands for the second light intensity in the second wavelength range for the pixel (m, n), $I_3^{mn}$ stands for the third light intensity in the third wavelength range for the pixel (m, n), $K_R$ is a constant coefficient for the first color component of the pixel (m, n), $K_G$ is a constant coefficient for the second color component of the pixel (m, n), and $K_B$ is a constant coefficient for the third color component of the pixel (m, n).

As discussed above, $Q_{1R}$, $Q_{1G}$, $Q_{1B}$, $Q_{2R}$, $Q_{2G}$, $Q_{2B}$, $Q_{3R}$, $Q_{3G}$, and $Q_{3B}$ are fixed values, and may be obtained by a calibration test. The three values $V_R^{mn}$, $V_G^{mn}$, and $V_B^{mn}$ may be measured by separating the image in each pixel of the plurality of pixels into three different color channels (e.g., a red color channel, a green color channel, and a blue color channel). Optionally, $V_R^{mn}$, $V_G^{mn}$, and $V_B^{mn}$ may be represented by grayscale values. Based on Equation (5), the first light intensity in the first wavelength range for the pixel (m, n), $I_1^{mn}$, the second light intensity in the second wavelength range for the pixel (m, n), $I_2^{mn}$, and the third light intensity in the third wavelength range for the pixel (m, n), $I_3^{mn}$, can be determined.

In some embodiments, an image sensor is used to detect a compound light reflected by or transmitted through a body part of the subject, thereby generating the plurality of images of the vessel of the subject. In determining the first light intensity in the first wavelength range, the second light intensity in the second wavelength range and the third light intensity in the third wavelength range, parameters of the image sensor are maintained substantially unchanged. For example, parameters affecting the RGB values of an output image of the image sensor, including aperture, exposure time, focal length, and gain, are maintained substantially unchanged in the process of determining the first light intensity, the second light intensity and the third light intensity. Frame rate can be adjusted as long as the frame interval is greater than the exposure time.

Further, Equation (5) can be expressed as follows:

$$\tilde{Q}\tilde{I}^{mn} = e^{\begin{pmatrix} \frac{V_R^{mn}}{K_R} \\ \frac{V_G^{mn}}{K_G} \\ \frac{V_B^{mn}}{K_B} \end{pmatrix}^{mn}}, \tilde{Q} = \begin{pmatrix} Q_{1R} & Q_{2R} & Q_{3R} \\ Q_{1G} & Q_{2G} & Q_{3G} \\ Q_{1B} & Q_{2B} & Q_{3B} \end{pmatrix}, \tilde{I} = \begin{pmatrix} I_1 \\ I_2 \\ I_3 \end{pmatrix}. \quad (6)$$

-continued $$\text{Thus, } \tilde{I}^{mn} = \tilde{Q}^{-1} e \begin{pmatrix} \frac{V_R^{mn}}{K_R} \\ \frac{V_G^{mn}}{K_G} \\ \frac{V_B^{mn}}{K_B} \end{pmatrix}^{mn}. \quad (7)$$

The first wavelength range, the second wavelength range, and the third wavelength range can be selected to have appropriate values, and an appropriate image sensor can be selected, so that |Q|≠0.

Upon determination of the first light intensity in the first wavelength range, the second light intensity in the second wavelength range, and the third light intensity in the third wavelength range, for each pixel of the plurality of pixels, the plurality of first grayscale images of the first wavelength range, the plurality of second grayscale images of the second wavelength range, and the plurality of third grayscale images of the third wavelength range, can be generated. The plurality of first grayscale images, the plurality of second grayscale images, and the plurality of third grayscale images can then be used for determining one or more physiological parameters of the subject. In one example, the plurality of first grayscale images are used to determine a vein pattern of the subject, the plurality of second grayscale images are used to determine a pulse wave signal of the subject, and the plurality of second grayscale images and the plurality of third grayscale images are used to determine a blood oxygen level of the subject.

In some embodiments, the method further includes providing the plurality of images of the vessel of the subject in response to illumination of the vessel to light of different wavelengths. Optionally, the method includes illuminating the vessel of the subject with a compound light having a first light of the first wavelength range, a second light of the second wavelength range, a third light of the third wavelength range; and detecting light reflected by or transmitted through a body part of the subject using an image sensor, thereby generating the plurality of images of the vessel of the subject. The light source used for illuminating the vessel of the subject in some embodiments is a single light source. Optionally, the light source used for illuminating the vessel of the subject includes a plurality of light emitting elements, e.g., a first light emitting element for emitting the first light of the first wavelength range, a second light emitting element for emitting the second light of the second wavelength range, and a third light emitting element for emitting the third light of the third wavelength range.

In some embodiments, the method further includes a calibration step to determine one or more of $Q_{1R}$, $Q_{1G}$, $Q_{1B}$, $Q_{2R}$, $Q_{2G}$, $Q_{2B}$, $Q_{3R}$, $Q_{3G}$, and $Q_{3B}$. Optionally, the method includes illuminating the vessel of the subject with a first reference light of the first wavelength range and determining a first reference quantum efficiency of the first color component of a pixel within the first wavelength range, a second reference quantum efficiency of the second color component of the pixel within the first wavelength range, and a third reference quantum efficiency of the third color component of the pixel within the first wavelength range. In one example, the first reference quantum efficiency is $Q_{1R}$, the second reference quantum efficiency is $Q_{1G}$, and the third reference quantum efficiency is $Q_{1B}$. Optionally, the method includes illuminating the vessel of the subject with a second reference light of the second wavelength range and determining a fourth reference quantum efficiency of the first color component of the pixel within the second wavelength range, a fifth reference quantum efficiency of the second color component of the pixel within the second wavelength range, and a sixth reference quantum efficiency of the third color component of the pixel within the second wavelength range. In another example, the fourth reference quantum efficiency is $Q_{2R}$, the fifth reference quantum efficiency is $Q_{2G}$, and the sixth reference quantum efficiency is $Q_{2B}$. Optionally, the method includes illuminating the vessel of the subject with a third reference light of the third wavelength range and determining a seventh reference quantum efficiency of the first color component of the pixel within the third wavelength range, an eighth reference quantum efficiency of the second color component of the pixel within the third wavelength range, and a ninth reference quantum efficiency of the third color component of the pixel within the third wavelength range. In another example, the seventh reference quantum efficiency is $Q_{3R}$, the eighth reference quantum efficiency is $Q_{3G}$, and the ninth reference quantum efficiency is $Q_{3B}$.

Various appropriate methods may be used for detecting blood oxygen levels. In one example, a plurality of images of a body part of a subject (e.g., skin) can be captured using an image sensor to record the reflection or transmission of light through an anatomical extremity, such as a human finger. Image characteristics corresponding to the plurality of first grayscale images at a first wavelength range (e.g., a first wavelength) can be compared with image characteristics corresponding to the plurality of second grayscale images at a second wavelength range (e.g., a second wavelength). The second wavelength is substantially distinct from the first wavelength. Blood oxygen level can be determined based on comparing the image characteristics.

In one example, oxygen saturation of a subject can be determined using an image sensor. A user can place his/her finger in proximity to the image sensor and a video or picture sequence can be captured. Image analysis and signal processing techniques can then be used on the captured sequence to process and extract oxygen saturation (SpO$_2$). The processing can be done either in real-time, such as while the picture sequence is being captured, or can be done off-line after the picture sequence has been captured.

In another example, SpO$_2$ can be determined according to:

$$SpO_2 = \frac{C_0}{C_0 + C_r}; \quad (8)$$

wherein SpO$_2$ stands for oxygen saturation, $C_0$ stands for oxygenated hemoglobin concentration, and Cr stands for deoxyhemoglobin concentration. According to Beer-Lambert's law for absorption of light through materials:

$$I_{out} = I_{in} * 10^{-(\alpha_0 C_0 + \alpha_r C_r)l} \quad (9);$$

for light with wavelength 1 and where $I_{in}$ is intensity of light passed through an artery of thickness 1, $I_{out}$ is intensity of light exiting the artery, $\alpha_0$ is the absorption coefficient of oxygenated blood at wavelength λ, and $\alpha_r$ is the absorption coefficient of deoxygenated blood at wavelength λ. In order to solve for 2 variables, namely variables $C_0$ and $C_r$, a differential technique wherein 2 wavelengths of light can be used where:

$$I_1 = I_{in1} * 10^{-(\alpha_{01} C_0 + \alpha_{r1} C_r)l} \quad (10);$$

at wavelength λ1, and $$I_2 = I_{in2} * 10^{-(\alpha_{02}C_0 + \alpha_{r2}C_r)l} \quad (11);$$

at wavelength λ2.

Thus, $$\frac{C_0}{C_0 + C_r} = \frac{\alpha_{r2}R - \alpha_{r1}}{(\alpha_{r2} - \alpha_{02}) - (\alpha_{r1} - \alpha_{01})}; \quad (12)$$

wherein $$R = \frac{\log_{10}\left(\frac{I_1}{I_{in1}}\right)}{\log_{10}\left(\frac{I_2}{I_{in2}}\right)}. \quad (13)$$

The value of R can be calculated by measuring the voltages at the output of photodiodes/pixels in the image sensor:

$$R = \frac{\log_{10}\left(\frac{V_{ac} + V_{dc}}{V_{dc}}\right) \text{ for } \lambda 1}{\log_{10}\left(\frac{V_{ac} + V_{dc}}{V_{dc}}\right) \text{ for } \lambda 2}. \quad (14)$$

Accordingly, the oxygen saturation can be determined.

Various appropriate methods may be used for detecting pulse wave signals. In one example, the pulse wave signals are detected by Photoplethysmography imaging (PPGi). In PPG imaging, backscattered light from a tissue is analyzed. When light irradiates on the tissue, a portion of that light scatters within the tissue, then interacts with the chromophores in the blood, and eventually is scattered back through the tissue surface (e.g., skin). When observed over time, this light-tissue interaction superimposes a weak AC modulation that is approximately 1-2% compared to the total amount of light reflected from the tissue. The small AC signal of this back-scattered light can be analyzed to obtain information regarding the position, relative blood volume, and relative blood concentration of the arterial circulation. Images generated from this information provide a method to assess pathologies involving changes to tissue blood flow and pulse rate including: tissue perfusion; cardiovascular health; wounds such as ulcers; peripheral arterial disease, and respiratory health. In one example, a near infrared light is used as illumination source to take advantage of the increased photon penetration into the tissue at this wavelength. A common setup includes positioning the light source near the target tissue to be imaged. This usually requires high dynamic range and low-light sensitive sensors to detect the PPG signal.

Various appropriate methods may be used for recognizing vein patterns. In one example, the vein pattern of a subject may be recognized by irradiating a body part of the subject with a near infrared light. Light is reflected by or transmits through the body part, after the light diffusing through the body part. The deoxidized hemoglobin in the vein vessels absorb the infrared ray, thereby reducing the reflection rate or transmission rate and causing the veins to appear as a black pattern. In one example, the vein pattern is verified against a preregistered pattern to authenticate a subject.

In another aspect, the present disclosure provides an apparatus for measuring one or more physiological parameters of a subject using a plurality of images of a vessel of the subject provided in response to illumination of the vessel to light of different wavelengths. In some embodiments, the apparatus includes a memory; and one or more processors. The memory and the one or more processors are connected with each other. In some embodiments, the memory stores computer-executable instructions for controlling the one or more processors to convert each of the plurality of images of the vessel into at least two grayscale images, thereby generating a plurality of first grayscale images of a first wavelength range and a plurality of second grayscale images of a second wavelength range, the first wavelength range and the second wavelength range being different from each other; and determine the one or more physiological parameters of the subject based on at least the plurality of first grayscale images and the plurality of second grayscale images.

Figure 5:
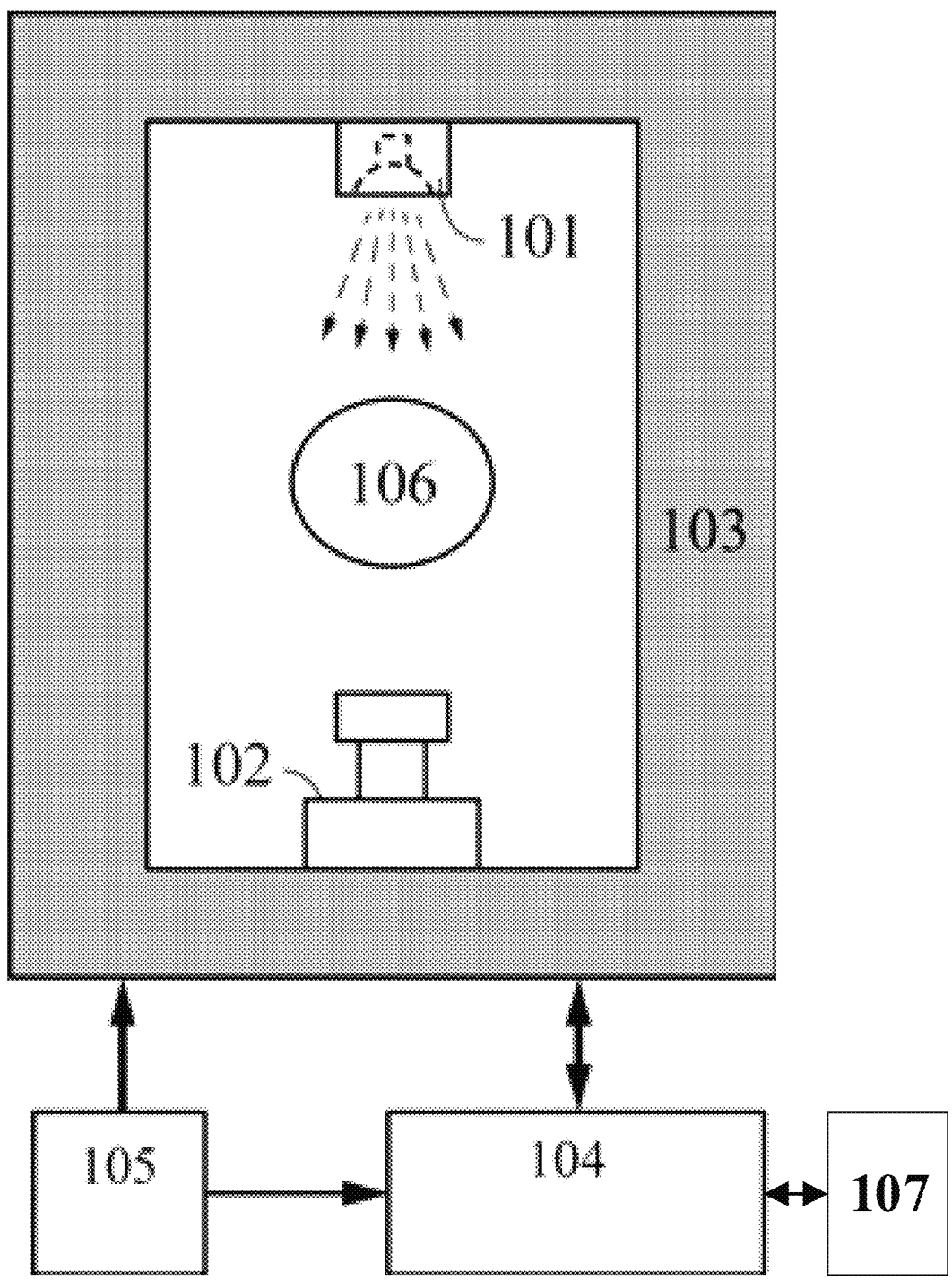
FIG. 5 is a schematic diagram illustrating an apparatus for measuring one or more physiological parameters of a subject in some embodiments according to the present disclosure.
Figure 6:
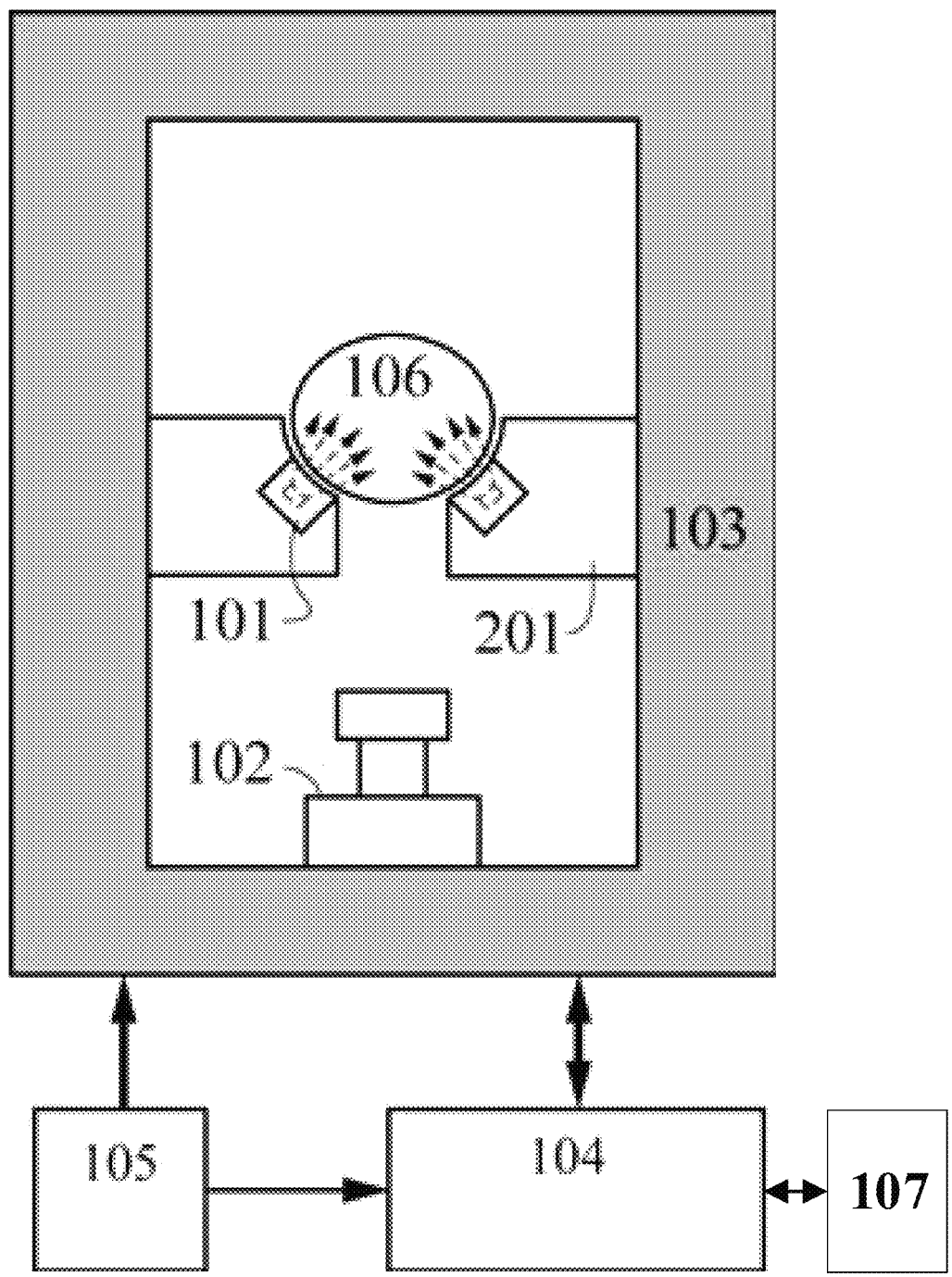
FIG. 6 is a schematic diagram illustrating an apparatus for measuring one or more physiological parameters of a subject in some embodiments according to the present disclosure.

FIG. 5 is a schematic diagram illustrating an apparatus for measuring one or more physiological parameters of a subject in some embodiments according to the present disclosure. Referring to FIG. 5, the apparatus in some embodiments includes a processor 104 and a memory 107 connected with each other. The memory 107 stores computer-executable instructions for controlling the processor 104 to perform the functions described above. FIG. 6 is a schematic diagram illustrating an apparatus for measuring one or more physiological parameters of a subject in some embodiments according to the present disclosure. Referring to FIG. 6, the apparatus in some embodiments includes a processor 104 and a memory 107 connected with each other. The memory 107 stores computer-executable instructions for controlling the processor 104 to perform the functions described above.

Various appropriate memories may be used in the present apparatus. Examples of appropriate memories include, but are not limited to, various types of processor-readable media such as random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or optical data storage, registers, magnetic disk or tape, optical storage media such as compact disk (CD) or DVD (digital versatile disk), and other non-transitory media. Optionally, the memory is a non-transitory memory. Various appropriate processors may be used in the present apparatus. Examples of appropriate processors include, but are not limited to, a general-purpose processor, a central processing unit (CPU), a microprocessor, a digital signal processor (DSP), a controller, a microcontroller, a state machine, etc.

Referring to FIG. 5, the apparatus in some embodiments further includes a light source 101 configured to emit light of multiple wavelengths, an image sensor 102 below the light source 101, and a body 103 forming a chamber having an opening on a lateral side. The image sensor 102 may be a color image sensor. The chamber formed by the body 103 prevents ambient light from interfering with the light detection of the image sensor 102. A body part 106 may be placed into the chamber through the opening on the lateral side of the body 103. The body part 106 may be placed between the light source 101 and the image sensor 102, so that the image sensor 102 may detect light transmitted through the body part 106 of the subject. The processor 104 is configured to acquire from the image sensor 102 a plurality of images of a vessel of the subject in response to illumination of the vessel to light of different wavelengths. The apparatus further includes a power source 105 configured to provide power supply for the light source 101, the image sensor 102, the memory 107, and the processor 104.

Referring to FIG. 6, the apparatus in some embodiments further includes a support 201 configured to support a body part 106 of the subject. Similar to the apparatus as shown in FIG. 5, the apparatus in FIG. 6 also includes a light source 101 configured to emit light of multiple wavelengths, an image sensor 102 below the light source 101, and a body 103 forming a chamber having an opening on a lateral side. The image sensor 102 may be a color image sensor. The chamber formed by the body 103 prevents ambient light from interfering with the light detection of the image sensor 102. A body part 106 may be placed into the chamber through the opening on the lateral side of the body 103. In the apparatus as shown in FIG. 6, the light source 101 is configured to emit light upwards, toward the body part 106 placed on the support 201. Optionally, the body part 106 is placed in close proximity to the light source 101. The image sensor 102 placed below the body part 106 is configured to detect light reflected by the body part 106 of the subject. The processor 104 is configured to acquire from the image sensor 102 a plurality of images of a vessel of the subject in response to illumination of the vessel to light of different wavelengths. The apparatus further includes a power source 105 configured to provide power supply for the light source 101, the image sensor 102, the memory 107, and the processor 104.

In some embodiments, the light source 101 is configured to illuminate a vessel (in the body part 106) of the subject with a compound light having a first light of the first wavelength range and a second light of the second wavelength range. Optionally, the first wavelength range and the second wavelength range are in a wavelength range of near infrared light and visible light. In one example, the first wavelength range is a wavelength range of a near infrared light, and the second wavelength range is a wavelength range of a visible light. In another example, the first wavelength range is a wavelength range of a near infrared light, and the second wavelength range is a wavelength range of a near infrared light. Optionally, the first wavelength range is between approximately 760 nm and approximately 850 nm; and the second wavelength range is between approximately 850 nm and approximately 960 nm. Optionally, the first wavelength range is between approximately 760 nm and approximately 850 nm; and the second wavelength range is between approximately 530 nm and approximately 660 nm. Optionally, the first wavelength range is between approximately 850 nm and approximately 960 nm; and the second wavelength range is between approximately 530 nm and approximately 660 nm.

In some embodiments, the light source 101 is configured to illuminate a vessel (in the body part 106) of the subject with a compound light having a first light of the first wavelength range, a second light of the second wavelength range, a third light of the third wavelength range. Optionally, the first wavelength range and the second wavelength range are in a wavelength range of near infrared light, and the third wavelength range is in a wavelength range of visible light. Optionally, the first wavelength range is between approximately 760 nm and approximately 850 nm; the second wavelength range is between approximately 850 nm and approximately 960 nm; and the third wavelength range is between approximately 530 nm and approximately 660 nm. The absorption peak for deoxyhemoglobin is approximately 760 nm. The absorption peak for oxygenated hemoglobin is approximately 910 nm. Thus, grayscale images taken at approximately 760 nm and approximately 660 nm may be used for detecting blood oxygen level (660 nm as the reference). Grayscale images taken at approximately 760 nm may be used for detecting vein pattern. Grayscale images taken at approximately 910 nm may be used for detecting pulse wave signals.

Optionally, the light source 101 is a single light source capable of simultaneously emitting the first light of the first wavelength range and the second light of the second wavelength range. Optionally, the light source 101 is a single light source capable of simultaneously emitting the first light of the first wavelength range, the second light of the second wavelength range, the third light of the third wavelength range. In one example, the light source 101 includes a white light and a plurality of fluorescent/phosphor layers. The plurality of fluorescent/phosphor layers are respectively configured to emit light of different wavelengths upon irradiation of white light. In another example, the light source 101 includes a white light and a plurality of color filter blocks. The plurality of color filter blocks are respectively configured to transmit light of different wavelengths upon irradiation of white light. In another example, light source 101 includes a plurality of light emitting diodes respectively configured to emit light of different wavelengths.

Optionally, the light source 101 includes a plurality of light emitting elements (e.g., light emitting diodes) respectively configured to emit light of different wavelengths. Optionally, the light source 101 includes at least two light emitting elements, one configured to emit the first light of the first wavelength range and the other configured to emit the second light of the second wavelength range. Optionally, the light source 101 includes three light emitting elements, the first configured to emit the first light of the first wavelength range, the second configured to emit the second light of the second wavelength range, and the third configured to emit the third light of the third wavelength range.

The image sensor 102 is configured to detecting the compound light reflected by or transmitted through a body part of the subject, thereby generating the plurality of images of the vessel of the subject. Optionally, the image sensor 102 is a single image sensor capable of detecting the compound light having at least the first light of the first wavelength range and the second light of the second wavelength range. Optionally, the image sensor 102 is a single image sensor capable of detecting the compound light having the first light of the first wavelength range, the second light of the second wavelength range, the third light of the third wavelength range.

Various appropriate image sensors may be used in the present apparatus. Examples of appropriate image sensors include a charged coupled device (CCD) image sensor and a complementary metal-oxide semiconductor (CMOS) image sensor. Optionally, the image sensor 102 is a color image sensor capable of detecting different colors, e.g., red color, green color, and blue color. Optionally, the image sensor 102 is capable of detecting signals in a long wavelength range, e.g., up to 1050 nm. Optionally, the image sensor 102 has a frame rate of at least 8 fps, e.g., greater than 25 fps.

In some embodiments, the memory further stores computer-executable instructions for controlling the one or more processors to determine a first value of a first color component, a second value of a second color component, and a third value of a third color component for each pixel of a plurality of pixels of each of the plurality of images; determine a first light intensity in the first wavelength range and a second light intensity in the second wavelength range for each pixel of the plurality of pixels, based on the first value, the second value, and the third value; and generate the plurality of first grayscale images of the first wavelength range based on the first light intensity in each pixel of the plurality of pixels and the plurality of second grayscale images of the second wavelength range based on the second light intensity in each pixel of the plurality of pixels.

In some embodiments, the memory further stores computer-executable instructions for controlling the one or more processors to determine the first light intensity in the first wavelength range and the second light intensity in the second wavelength range according to Equation (1):

$$\begin{cases} Q_{1R}I_1^{mn} + Q_{2R}I_2^{mn} = e^{\left(\frac{V_R^{mn}}{K_R}\right)} \\ Q_{1G}I_1^{mn} + Q_{2G}I_2^{mn} = e^{\left(\frac{V_G^{mn}}{K_G}\right)}; \\ Q_{1B}I_1^{mn} + Q_{2B}I_2^{mn} = e^{\left(\frac{V_B^{mn}}{K_B}\right)} \end{cases} \quad (1)$$

wherein $V_R^{mn}$ stands for the first value of a first color component for a pixel (m, n) in a plurality of pixels having m rows and n columns of pixels, $V_G^{mn}$ stands for the second value of a second color component for the pixel (m, n), $V_B^{mn}$ stands for the third value of a third color component for the pixel (m, n), $Q_{1R}$ stands for a first reference quantum efficiency of the first color component of the pixel (m, n) within the first wavelength range, $Q_{1G}$ stands for a second reference quantum efficiency of the second color component of the pixel (m, n) within the first wavelength range, $Q_{1B}$ stands for a third reference quantum efficiency of the third color component of the pixel (m, n) within the first wavelength range, $Q_{2R}$ stands for a fourth reference quantum efficiency of the first color component of the pixel (m, n) within the second wavelength range, $Q_{2G}$ stands for a fifth reference quantum efficiency of the second color component of the pixel (m, n) within the second wavelength range, $Q_{2B}$ stands for a sixth reference quantum efficiency of the third color component of the pixel (m, n) within the second wavelength range, $I_1^{mn}$ stands for the first light intensity in the first wavelength range for the pixel (m, n), $I_2^{mn}$ stands for the second light intensity in the second wavelength range for the pixel (m, n), $K_R$ is a constant coefficient for the first color component of the pixel (m, n), $K_G$ is a constant coefficient for the second color component of the pixel (m, n), and $K_B$ is a constant coefficient for the third color component of the pixel (m, n).

As discussed above, $Q_{1R}$, $Q_{1G}$, $Q_{1B}$, $Q_{2R}$, $Q_{2G}$, and $Q_{2B}$ are fixed values, and may be obtained by a calibration test. The three values $V_R^{mn}$, $V_G^{mn}$, and $V_B^{mn}$ may be measured by separating the image in each pixel of the plurality of pixels into three different color channels (e.g., a red color channel, a green color channel, and a blue color channel). Optionally, $V_R^{mn}$, $V_G^{mn}$, and $V_B^{mn}$ may be represented by grayscale values. Based on Equation (1), the first light intensity in the first wavelength range for the pixel (m, n), $I_1^{mn}$, and the second light intensity in the second wavelength range for the pixel (m, n), $I_2^{mn}$, can be determined.

In some embodiments, an image sensor is used to detect a compound light reflected by or transmitted through a body part of the subject, thereby generating the plurality of images of the vessel of the subject. In determining the first light intensity in the first wavelength range and the second light intensity in the second wavelength range, parameters of the image sensor are maintained substantially unchanged. For example, parameters affecting the RGB values of an output image of the image sensor, including aperture, exposure time, focal length, and gain, are maintained substantially unchanged in the process of determining the first light intensity and the second light intensity. Frame rate can be adjusted as long as the frame interval is greater than the exposure time.

In some embodiments, the memory further stores computer-executable instructions for controlling the one or more processors to convert each of the plurality of images of the vessel into three grayscale images, thereby generating the plurality of first grayscale images of the first wavelength range, the plurality of second grayscale images of the second wavelength range, and a plurality of third grayscale images of a third wavelength range, the first wavelength range, the second wavelength range, and the third wavelength range being different from each other; and determining at least two physiological parameters of the subject based on the plurality of first grayscale images, the plurality of second grayscale images, and the plurality of third grayscale images.

Optionally, the memory further stores computer-executable instructions for controlling the one or more processors to determine a first value of a first color component, a second value of a second color component, and a third value of a third color component for each pixel of a plurality of pixels of each of the plurality of images; determine a first light intensity in the first wavelength range, a second light intensity in the second wavelength range, and a third light intensity in the third wavelength range for each pixel of the plurality of pixels, based on the first value, the second value, and the third value; and generate the plurality of first grayscale images of the first wavelength range based on the first light intensity in each pixel of the plurality of pixels, the plurality of second grayscale images of the second wavelength range based on the second light intensity in each pixel of the plurality of pixels, and the plurality of third grayscale images of the third wavelength range based on the third light intensity in each pixel of the plurality of pixels.

In some embodiments, the memory further stores computer-executable instructions for controlling the one or more processors to determine the first light intensity in the first wavelength range, the second light intensity in the second wavelength range, and the third light intensity in the third wavelength range according to Equation (5):

$$\begin{cases} Q_{1R}I_1^{mn} + Q_{2R}I_2^{mn} + Q_{3R}I_3^{mn} = e^{\left(\frac{V_R^{mn}}{K_R}\right)} \\ Q_{1G}I_1^{mn} + Q_{2G}I_2^{mn} + Q_{3G}I_3^{mn} = e^{\left(\frac{V_G^{mn}}{K_G}\right)}; \\ Q_{1B}I_1^{mn} + Q_{2B}I_2^{mn} + Q_{3B}I_3^{mn} = e^{\left(\frac{V_B^{mn}}{K_B}\right)} \end{cases} \quad (5)$$

wherein $V_R^{mn}$ stands for the first value of a first color component for a pixel (m, n) in a plurality of pixels having m rows and n columns of pixels, $V_G^{mn}$ stands for the second value of a second color component for the pixel (m, n), $V_B^{mn}$ stands for the third value of a third color component for the pixel (m, n), $Q_{1R}$ stands for a first reference quantum efficiency of the first color component of the pixel (m, n) within the first wavelength range, $Q_{1G}$ stands for a second reference quantum efficiency of the second color component of the pixel (m, n) within the first wavelength range, $Q_{1B}$ stands for a third reference quantum efficiency of the third color component of the pixel (m, n) within the first wavelength range, $Q_{2R}$ stands for a fourth reference quantum efficiency of the first color component of the pixel (m, n) within the second wavelength range, $Q_{2G}$ stands for a fifth reference quantum efficiency of the second color component of the pixel (m, n) within the second wavelength range, $Q_{2B}$ stands for a sixth reference quantum efficiency of the third color component of the pixel (m, n) within the second wavelength range, $Q_{3R}$ stands for a seventh reference quantum efficiency of the first color component of the pixel (m, n) within the third wavelength range, $Q_{3G}$ stands for an eighth reference quantum efficiency of the second color component of the pixel (m, n) within the third wavelength range, $Q_{3B}$ stands for a ninth reference quantum efficiency of the third color component of the pixel (m, n) within the third wavelength range, $I_1^{mn}$ stands for the first light intensity in the first wavelength range for the pixel (m, n), $I_2^{mn}$ stands for the second light intensity in the second wavelength range for the pixel (m, n), $I_3^{mn}$ stands for the third light intensity in the third wavelength range for the pixel (m, n), $K_R$ is a constant coefficient for the first color component of the pixel (m, n), $K_G$ is a constant coefficient for the first color component of the pixel (m, n), and $K_B$ is a constant coefficient for the first color component of the pixel (m, n).

As discussed above, $Q_{1R}$, $Q_{1G}$, $Q_{1B}$, $Q_{2R}$, $Q_{2G}$, $Q_{2B}$, $Q_{3R}$, $Q_{3G}$, and $Q_{3B}$ are fixed values, and may be obtained by a calibration test. The three values $V_R^{mn}$, $V_G^{mn}$, and $V_B^{mn}$ may be measured by separating the image in each pixel of the plurality of pixels into three different color channels (e.g., a red color channel, a green color channel, and a blue color channel). Optionally, $V_R^{mn}$, $V_G^{mn}$, and $V_B^{mn}$ may be represented by grayscale values. Based on Equation (5), the first light intensity in the first wavelength range for the pixel (m, n), $I_1^{mn}$, the second light intensity in the second wavelength range for the pixel (m, n), $I_2^{mn}$, and the third light intensity in the third wavelength range for the pixel (m, n), $I_3^{mn}$, can be determined.

In some embodiments, an image sensor is used to detect a compound light reflected by or transmitted through a body part of the subject, thereby generating the plurality of images of the vessel of the subject. In determining the first light intensity in the first wavelength range, the second light intensity in the second wavelength range and the third light intensity in the third wavelength range, parameters of the image sensor are maintained substantially unchanged. For example, parameters affecting the RGB values of an output image of the image sensor, including aperture, exposure time, focal length, and gain, are maintained substantially unchanged in the process of determining the first light intensity, the second light intensity and the third light intensity. Frame rate can be adjusted as long as the frame interval is greater than the exposure time.

In some embodiments, the apparatus is a stand-alone medical monitoring apparatus. In some embodiments, the apparatus for measuring a plurality of physiological parameters of a subject is integrated into a display apparatus, e.g., a mobile phone, a laptop, a tablet. In some embodiments, the apparatus for measuring a plurality of physiological parameters of a subject is integrated into a health gadget. In some embodiments, the apparatus for measuring a plurality of physiological parameters of a subject is integrated into a fitness equipment.

In another aspect, the present disclosure provides a computer-program product including a non-transitory tangible computer-readable medium having computer-readable instructions thereon. In some embodiments, the computer-readable instructions are executable by a processor to cause the processor to perform converting each of a plurality of images of a vessel of a subject provided in response to illumination of the vessel to light of different wavelengths into at least two grayscale images, thereby generating a plurality of first grayscale images of a first wavelength range and a plurality of second grayscale images of a second wavelength range, the first wavelength range and the second wavelength range being different from each other; and determining one or more physiological parameters of the subject based on at least the plurality of first grayscale images and the plurality of second grayscale images.

In some embodiments, the computer-readable instructions are executable by a processor to cause the processor to further perform determining a first value of a first color component, a second value of a second color component, and a third value of a third color component for each pixel of a plurality of pixels of each of the plurality of images; determining a first light intensity in the first wavelength range and a second light intensity in the second wavelength range for each pixel of the plurality of pixels, based on the first value, the second value, and the third value; and generating the plurality of first grayscale images of the first wavelength range based on the first light intensity in each pixel of the plurality of pixels and the plurality of second grayscale images of the second wavelength range based on the second light intensity in each pixel of the plurality of pixels.

In some embodiments, the computer-readable instructions are executable by a processor to cause the processor to further perform converting each of the plurality of images of the vessel into three grayscale images, thereby generating the plurality of first grayscale images of the first wavelength range, the plurality of second grayscale images of the second wavelength range, and a plurality of third grayscale images of a third wavelength range, the first wavelength range, the second wavelength range, and the third wavelength range being different from each other; and determining at least two physiological parameters of the subject based on the plurality of first grayscale images, the plurality of second grayscale images, and the plurality of third grayscale images.

In some embodiments, the computer-readable instructions are executable by a processor to cause the processor to further perform determining a first value of a first color component, a second value of a second color component, and a third value of a third color component for each pixel of a plurality of pixels of each of the plurality of images; determining a first light intensity in the first wavelength range, a second light intensity in the second wavelength range, and a third light intensity in the third wavelength range for each pixel of the plurality of pixels, based on the first value, the second value, and the third value; and generating the plurality of first grayscale images of the first wavelength range based on the first light intensity in each pixel of the plurality of pixels, the plurality of second grayscale images of the second wavelength range based on the second light intensity in each pixel of the plurality of pixels, and the plurality of third grayscale images of the third wavelength range based on the third light intensity in each pixel of the plurality of pixels.

The foregoing description of the embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to exemplary embodiments of the invention does not imply a limitation on the invention, and no such limitation is to be inferred. The invention is limited only by the spirit and scope of the appended claims. Moreover, these claims may refer to use "first", "second", etc. following with noun or element. Such terms should be understood as a nomenclature and should not be construed as giving the limitation on the number of the elements modified by such nomenclature unless specific number has been given. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A method for determining one or more physiological parameters of a subject, comprising:
    providing a plurality of images of a vessel of the subject in response to illumination of the vessel to light of different wavelengths;
    converting each of the plurality of images of the vessel into at least two grayscale images, thereby generating a plurality of first grayscale images of a first wavelength range and a plurality of second grayscale images of a second wavelength range, the first wavelength range and the second wavelength range being different from each other; and
    determining the one or more physiological parameters of the subject based on at least the plurality of first grayscale images and the plurality of second grayscale images;
    wherein converting each of the plurality of images of the vessel into at least two grayscale images comprises:
    determining a first value of a first color component, a second value of a second color component, and a third value of a third color component for each pixel of a plurality of pixels of each of the plurality of images;
    determining a first light intensity in the first wavelength range and a second light intensity in the second wavelength range for each pixel of the plurality of pixels, based on the first value, the second value, and the third value; and
    generating the plurality of first grayscale images of the first wavelength range based on the first light intensity in each pixel of the plurality of pixels and the plurality of second grayscale images of the second wavelength range based on the second light intensity in each pixel of the plurality of pixels.

2. The method of claim 1, wherein determining the first light intensity in the first wavelength range and the second light intensity in the second wavelength range is performed based on Equation (1):

$$\begin{cases} Q_{1R}I_1^{mn} + Q_{2R}I_2^{mn} = e^{\left(\frac{V_R^{mn}}{K_R}\right)} \\ Q_{1G}I_1^{mn} + Q_{2G}I_2^{mn} = e^{\left(\frac{V_G^{mn}}{K_G}\right)} \\ Q_{1B}I_1^{mn} + Q_{2B}I_2^{mn} = e^{\left(\frac{V_B^{mn}}{K_B}\right)} \end{cases} \quad (1)$$

wherein $V_R^{mn}$ stands for the first value of a first color component for a pixel (m, n) in a plurality of pixels having m rows and n columns of pixels, $V_G^{mn}$ stands for the second value of a second color component for the pixel (m, n), $V_B^{mn}$ stands for the third value of a third color component for the pixel (m, n), $Q_{1R}$ stands for a first reference quantum efficiency of the first color component of the pixel (m, n) within the first wavelength range, $Q_{1G}$ stands for a second reference quantum efficiency of the second color component of the pixel (m, n) within the first wavelength range, $Q_{1B}$ stands for a third reference quantum efficiency of the third color component of the pixel (m, n) within the first wavelength range, $Q_{2R}$ stands for a fourth reference quantum efficiency of the first color component of the pixel (m, n) within the second wavelength range, $Q_{2G}$ stands for a fifth reference quantum efficiency of the second color component of the pixel (m, n) within the second wavelength range, $Q_{2B}$ stands for a sixth reference quantum efficiency of the third color component of the pixel (m, n) within the second wavelength range, $I_1^{mn}$ stands for the first light intensity in the first wavelength range for the pixel (m, n), $I_2^{mn}$ stands for the second light intensity in the second wavelength range for the pixel (m, n), $K_R$ is a constant coefficient for the first color component of the pixel (m, n), $K_G$ is a constant coefficient for the first color component of the pixel (m, n), and $K_B$ is a constant coefficient for the first color component of the pixel (m, n).

3. The method of claim 1, wherein converting each of the plurality of images of the vessel into at least two grayscale images comprises converting each of the plurality of images of the vessel into three grayscale images, thereby generating the plurality of first grayscale images of the first wavelength range, the plurality of second grayscale images of the second wavelength range, and a plurality of third grayscale images of a third wavelength range, the first wavelength range, the second wavelength range, and the third wavelength range being different from each other; and
    wherein determining the one or more physiological parameters of the subject based on at least the plurality of first grayscale images and the plurality of second grayscale images comprises determining at least two physiological parameters of the subject based on the plurality of first grayscale images, the plurality of second grayscale images, and the plurality of third grayscale images.

4. The method of claim 3, wherein converting each of the plurality of images of the vessel into three grayscale images comprises:
    determining a first value of a first color component, a second value of a second color component, and a third value of a third color component for each pixel of a plurality of pixels of each of the plurality of images;
    determining a first light intensity in the first wavelength range, a second light intensity in the second wavelength range, and a third light intensity in the third wavelength range for each pixel of the plurality of pixels, based on the first value, the second value, and the third value; and generating the plurality of first grayscale images of the first wavelength range based on the first light intensity in each pixel of the plurality of pixels, the plurality of second grayscale images of the second wavelength range based on the second light intensity in each pixel of the plurality of pixels, and the plurality of third grayscale images of the third wavelength range based on the third light intensity in each pixel of the plurality of pixels.

5. The method of claim 4, wherein determining the first light intensity in the first wavelength range, the second light intensity in the second wavelength range, and the third light intensity in the third wavelength range is performed based on Equation (2):

$$\begin{cases} Q_{1R}I_1^{mn} + Q_{2R}I_2^{mn} + Q_{3R}I_3^{mn} = e^{\left(\frac{V_R^{mn}}{K_R}\right)} \\ Q_{1G}I_1^{mn} + Q_{2G}I_2^{mn} + Q_{3G}I_3^{mn} = e^{\left(\frac{V_G^{mn}}{K_G}\right)}; \\ Q_{1B}I_1^{mn} + Q_{2B}I_2^{mn} + Q_{3B}I_3^{mn} = e^{\left(\frac{V_B^{mn}}{K_B}\right)} \end{cases} \quad (2)$$

wherein $V_R^{mn}$ stands for the first value of a first color component for a pixel (m, n) in a plurality of pixels having m rows and n columns of pixels, $V_G^{mn}$ stands for the second value of a second color component for the pixel (m, n), $V_B^{mn}$ stands for the third value of a third color component for the pixel (m, n), $Q_{1R}$ stands for a first reference quantum efficiency of the first color component of the pixel (m, n) within the first wavelength range, $Q_{1G}$ stands for a second reference quantum efficiency of the second color component of the pixel (m, n) within the first wavelength range, $Q_{1B}$ stands for a third reference quantum efficiency of the third color component of the pixel (m, n) within the first wavelength range, $Q_{2R}$ stands for a fourth reference quantum efficiency of the first color component of the pixel (m, n) within the second wavelength range, $Q_{2G}$ stands for a fifth reference quantum efficiency of the second color component of the pixel (m, n) within the second wavelength range, $Q_{2B}$ stands for a sixth reference quantum efficiency of the third color component of the pixel (m, n) within the second wavelength range, $Q_{3R}$ stands for a seventh reference quantum efficiency of the first color component of the pixel (m, n) within the third wavelength range, $Q_{3G}$ stands for an eighth reference quantum efficiency of the second color component of the pixel (m, n) within the third wavelength range, $Q_{3B}$ stands for a ninth reference quantum efficiency of the third color component of the pixel (m, n) within the third wavelength range, $I_1^{mn}$ stands for the first light intensity in the first wavelength range for the pixel (m, n), $I_2^{mn}$ stands for the second light intensity in the second wavelength range for the pixel (m, n), $I_3^{mn}$ stands for the third light intensity in the third wavelength range for the pixel (m, n), $K_R$ is a constant coefficient for the first color component of the pixel (m, n), $K_G$ is a constant coefficient for the first color component of the pixel (m, n), and $K_B$ is a constant coefficient for the first color component of the pixel (m, n).

6. The method of claim 1, further comprising illuminating the vessel of the subject with a compound light having a first light of the first wavelength range, a second light of the second wavelength range, a third light of a third wavelength range; and detecting light reflected by or transmitted through a body part of the subject using an image sensor, thereby generating the plurality of images of the vessel of the subject.

7. The method of claim 1, further comprising at least one of:

(1) illuminating the vessel of the subject with a first reference light of the first wavelength range and determining a first reference quantum efficiency of the first color component of a pixel within the first wavelength range, a second reference quantum efficiency of the second color component of the pixel within the first wavelength range, and a third reference quantum efficiency of the third color component of the pixel within the first wavelength range;

(2) illuminating the vessel of the subject with a second reference light of the second wavelength range and determining a fourth reference quantum efficiency of the first color component of the pixel within the second wavelength range, a fifth reference quantum efficiency of the second color component of the pixel within the second wavelength range, and a sixth reference quantum efficiency of the third color component of the pixel within the second wavelength range; or (3) illuminating the vessel of the subject with a third reference light of a third wavelength range and determining a seventh reference quantum efficiency of the first color component of the pixel within the third wavelength range, an eighth reference quantum efficiency of the second color component of the pixel within the third wavelength range, and a ninth reference quantum efficiency of the third color component of the pixel within the third wavelength range.

8. The method of claim 1, wherein the first wavelength range and the second wavelength range are in a wavelength range of near infrared light and visible light.

9. The method of claim 3, wherein the first wavelength range is between approximately 760 nm and approximately 850 nm;

the second wavelength range is between approximately 850 nm and approximately 960 nm; and the third wavelength range is between approximately 530 nm and approximately 660 nm.

10. The method of claim 1, wherein the one or more physiological parameters of the subject comprise a vein pattern, a pulse wave signal, and a blood oxygen level of the subject.

11. An apparatus for measuring one or more physiological parameters of a subject using a plurality of images of a vessel of the subject provided in response to illumination of the vessel to light of different wavelengths, comprising:

a memory; and one or more processors;

wherein the memory and the one or more processors are connected with each other; and the memory stores computer-executable instructions for controlling the one or more processors to:

convert each of the plurality of images of the vessel into at least two grayscale images, thereby generating a plurality of first grayscale images of a first wavelength range and a plurality of second grayscale images of a second wavelength range, the first wavelength range and the second wavelength range being different from each other; and determine the one or more physiological parameters of the subject based on at least the plurality of first grayscale images and the plurality of second grayscale images;

wherein the apparatus further comprises:

a light source configured to illuminate a vessel of the subject with a compound light having at least a first light of the first wavelength range and a second light of the second wavelength range; and an image sensor configured to detecting the compound light reflected by or transmitted through a body part of the subject, thereby generating the plurality of images of the vessel of the subject.

12. The apparatus of claim 11, wherein the image sensor is a single image sensor capable of detecting the compound light having the first light of the first wavelength range and the second light of the second wavelength range.

13. The apparatus of claim 11, wherein the light source is a single light source capable of simultaneously emitting the first light of the first wavelength range and the second light of the second wavelength range.

14. The apparatus of claim 11, wherein the memory further stores computer-executable instructions for controlling the one or more processors to:

determine a first value of a first color component, a second value of a second color component, and a third value of a third color component for each pixel of a plurality of pixels of each of the plurality of images;

determine a first light intensity in the first wavelength range and a second light intensity in the second wavelength range for each pixel of the plurality of pixels, based on the first value, the second value, and the third value; and generate the plurality of first grayscale images of the first wavelength range based on the first light intensity in each pixel of the plurality of pixels and the plurality of second grayscale images of the second wavelength range based on the second light intensity in each pixel of the plurality of pixels.

15. The apparatus of claim 11, wherein the memory stores computer-executable instructions for controlling the one or more processors to:

convert each of the plurality of images of the vessel into three grayscale images, thereby generating the plurality of first grayscale images of the first wavelength range, the plurality of second grayscale images of the second wavelength range, and a plurality of third grayscale images of a third wavelength range, the first wavelength range, the second wavelength range, and the third wavelength range being different from each other; and determining at least two physiological parameters of the subject based on the plurality of first grayscale images, the plurality of second grayscale images, and the plurality of third grayscale images.

16. The apparatus of claim 15, wherein the memory further stores computer-executable instructions for controlling the one or more processors to:

determine a first value of a first color component, a second value of a second color component, and a third value of a third color component for each pixel of a plurality of pixels of each of the plurality of images;

determine a first light intensity in the first wavelength range, a second light intensity in the second wavelength range, and a third light intensity in the third wavelength range for each pixel of the plurality of pixels, based on the first value, the second value, and the third value; and generate the plurality of first grayscale images of the first wavelength range based on the first light intensity in each pixel of the plurality of pixels, the plurality of second grayscale images of the second wavelength range based on the second light intensity in each pixel of the plurality of pixels, and the plurality of third grayscale images of the third wavelength range based on the third light intensity in each pixel of the plurality of pixels.

17. The apparatus of claim 11, wherein the one or more physiological parameters of the subject comprise a vein pattern, a pulse wave signal, and a blood oxygen level of the subject.

18. A computer-program product comprising a non-transitory tangible computer-readable medium having computer-readable instructions thereon, the computer-readable instructions being executable by a processor to cause the processor to perform:

converting each of a plurality of images of a vessel of a subject provided in response to illumination of the vessel to light of different wavelengths into at least two grayscale images, thereby generating a plurality of first grayscale images of a first wavelength range and a plurality of second grayscale images of a second wavelength range, the first wavelength range and the second wavelength range being different from each other; and determining one or more physiological parameters of the subject based on at least the plurality of first grayscale images and the plurality of second grayscale images;

wherein converting each of the plurality of images of the vessel into at least two grayscale images comprises:

determining a first value of a first color component, a second value of a second color component, and a third value of a third color component for each pixel of a plurality of pixels of each of the plurality of images;

determining a first light intensity in the first wavelength range and a second light intensity in the second wavelength range for each pixel of the plurality of pixels, based on the first value, the second value, and the third value; and generating the plurality of first grayscale images of the first wavelength range based on the first light intensity in each pixel of the plurality of pixels and the plurality of second grayscale images of the second wavelength range based on the second light intensity in each pixel of the plurality of pixels.

* * * * *